US006350230B1

(12) United States Patent
Kontos

(10) Patent No.: US 6,350,230 B1
(45) Date of Patent: Feb. 26, 2002

(54) SEXUAL AID DEVICE

(76) Inventor: George Vlasios Kontos, 3909 Lake Des Allemands Dr., Harvey, LA (US) 70058

( * ) Notice: Subject to any disclaimer, the term of this patent is extended or adjusted under 35 U.S.C. 154(b) by 0 days.

(21) Appl. No.: 09/614,173

(22) Filed: Jul. 11, 2000

Related U.S. Application Data

(60) Provisional application No. 60/181,325, filed on Feb. 9, 2000, and provisional application No. 60/166,999, filed on Nov. 23, 1999.

(51) Int. Cl.$^{7}$ .................................................. A61F 5/00
(52) U.S. Cl. ........................................................ 600/38
(58) Field of Search .................... 600/38, 587; 128/842

(56) References Cited

U.S. PATENT DOCUMENTS 4,718,411 A * 1/1988 Stewart ........................ 600/38
5,063,939 A * 11/1991 Walston ...................... 128/842

OTHER PUBLICATIONS

Adam & Eve; Hi–Tech Rabbi Pearl Vibe; May 29, 1998; Adam & Eve Online.*
Toy Synopsis; Robo Suck; Oct. 24, 2001; Galaxy Internet Group.*
Toy Synopsis; Cyberskin Color Cock—Vibrating 7 inch; Oct. 24, 2001; Galaxy Internet Group.*

* cited by examiner

*Primary Examiner*—Eric F. Winakur
*Assistant Examiner*—Nikita Veniaminov

(57) ABSTRACT

A sexual aid device for producing sexual stimulation having an elongated upper member, an elongated lower member, a means for removably securing the upper and lower members together, a tube member, and a compression means for ejaculating liquid from the tube member. An upper end of the upper member has an aperture therethrough. The elongated lower member has a compartment therein for one or more batteries for powering the device. The tube member has a compressible liquid containment unit on a lower end thereof. A hollow neck member extends upward from the liquid containment unit, the hollow neck member being in fluid communication with the liquid containment unit. The neck member has an open upper end. During use the tube member is positioned inside the device such that the open upper end of the neck member is inserted in the aperture of the upper member. The compression means is configured and positioned to compress the liquid containment unit to thereby ejaculate liquid from the tube member. The device is preferably provided with a vibration means, a timing unit, and a heating element, all of which may be selectively used as needed when using the device to provide sexual stimulation. Methods of using the device are also provided.

26 Claims, 2 Drawing Sheets

SEXUAL AID DEVICE

CROSS REFERENCES TO RELATED APPLICATIONS

Applicant herein claims priority to U.S. Provisional Patent Application Ser. No. 60/181,325, which was filed in the United States Patent and Trademark Office on Feb. 9, 2000 and is pending, and to U.S. Provisional Patent Application Ser. No. 60/166,999, which was filed in the United States Patent and Trademark Office on Nov. 23, 1999 and is pending.

FIELD OF INVENTION

The present invention relates to sexual devices, and more particularly to a sexual aid device for producing sexual stimulation and replicating the act of male ejaculation.

BACKGROUND OF THE INVENTION

Dildos and the like are used to produce sexual stimulation. Dildos are typically shaped in the form of a male penis, and are produced in many shapes and configurations. Dildos are used to stimulate the Grafenberg ("G") spot, external genitalia, or for vaginal or anal penetration and stimulation of the user or partner. Some dildos incorporate vibrator mechanisms to enhance the sexual stimulation properties of the device. Devices incorporating such mechanisms are typically powered by internally stored batteries, which provide a safe source of electricity and do not hamper the portability and usability of the device.

As far as the inventor is aware, no attempts have been made to provide a dildo that replicates the act of male ejaculation. There is thus a need for a sexual aid device that overcomes the shortcomings of the prior art.

OBJECTS AND SUMMARY OF THE INVENTION

It is an object of the invention to provide a sexual aid device in the form of a dildo that produces enhanced sexual stimulation.

It is another object of the invention to provide a sexual aid device in the form of a dildo that produces enhanced sexual stimulation in part by replicating the act of male ejaculation.

It is another object of the invention to provide a sexual aid device in the form of a dildo that can be programmed to replicate the act of male ejaculation upon expiration of a selected or a random time interval.

It is yet another object of the invention to provide a sexual aid device in the form of a dildo that produces enhanced sexual stimulation by combining replication of the act of male ejaculation with other operational enhancements such as heat and vibration.

These and other objects and advantages of the invention shall become apparent from the following general and preferred description of the invention.

Accordingly, a sexual aid device is provide comprising an elongated upper member, an elongated lower member, a means for removably securing the upper and lower members together, a tube member, and a compression means for ejaculating liquid from the tube member. The outer shell of the device is preferably covered by a coating of rubber, silicon, plastic or the like to provide for a more realistic, flesh-like feeling and sensation. The elongated upper member has a substantially hollow interior. An upper end of the upper member has an aperture therethrough. The elongated lower member has a compartment therein for receiving and holding one or more batteries for powering the device. The tube member has a compressible liquid containment unit on a lower end thereof. A hollow neck member extends upward from the liquid containment unit, the hollow neck member being in fluid communication with the liquid containment unit. The neck member has an open upper end, which is preferably sealed with a one way valve to prevent inadvertent loss of liquid from the liquid containment unit. During use the tube member is positioned inside the device such that the open upper end of the neck member is inserted in the aperture of the upper member.

The compression means is preferably positioned in the upper end of the lower member. The compression means is configured and positioned to compress the liquid containment unit when electrical connection is selectively established between the compression means and a battery in the lower member. When the compression means compresses the liquid containment unit, liquid stored in the liquid containment unit is ejaculated or projected through the open upper end of the tube member. In a preferred embodiment, the compression means is a DC powered solenoid pinch valve. A one-way valve is preferably positioned in the aperture to allow liquid in the tube member to exit the aperture while preventing the ejected liquid from reentering the aperture. The device is preferably provided with a vibration means, a timing unit, and a heating element, all of which may be selectively used as needed when using the device to provide sexual stimulation. Methods of using the device are also provided.

PREFERRED EMBODIMENTS OF THE INVENTION

Figures 1, 2, 3, 4, 5, 6:
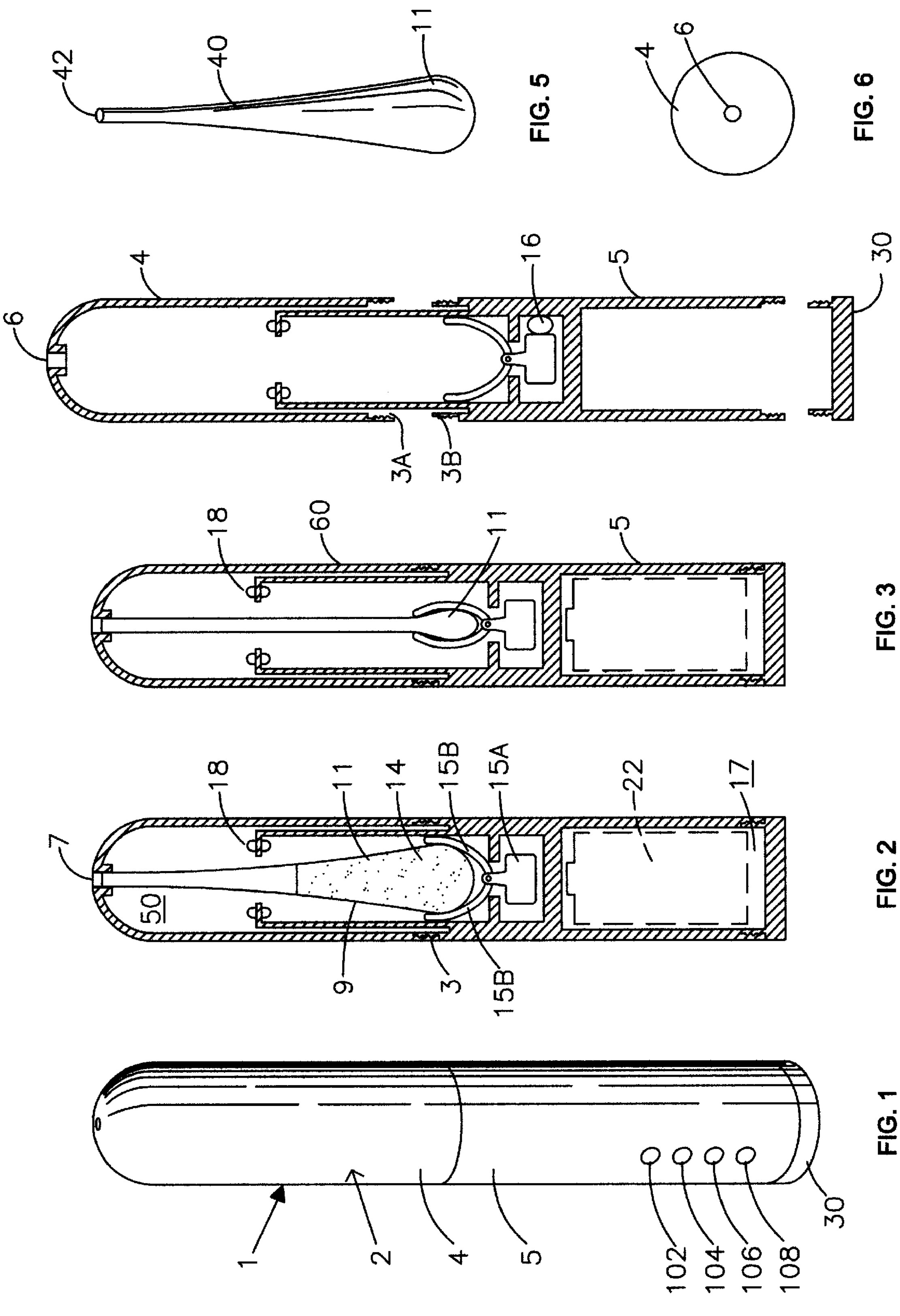
FIG. 1 is a perspective side view of one preferred embodiment of the invention.
FIG. 2 is a cross-sectional side view of one preferred embodiment of the invention illustrating internal mechanisms of the invention and illustrating the invention in a ready to ejaculate condition.
FIG. 3 is a cross-sectional side view of one preferred embodiment of the invention illustrating the invention in an ejaculated condition.
FIG. 4 is a cross-sectional side view of one preferred embodiment of the invention showing the tube member removed from the device.
FIG. 5 is a side perspective view showing external features of a preferred embodiment of the tube member.
FIG. 6 is a top view of one preferred embodiment of the invention.

A sexual aid device 1 is provided that is designed to be shaped like a male penis, or a dildo, and is to be used to stimulate the Grafenberg spot ("G-spot") of a woman, external genitalia, or for vaginal or anal penetration and stimulation of the user or partner. FIG. 1 shows external features of a preferred embodiment of the device 1. As shown in FIG. 2, the sexual aid device 1 for producing sexual stimulation comprises, generally, an elongated upper member 4, an elongated lower member, a means 3A, 3B for removably securing the upper 4 and lower 5 members together, a tube member 9, and a compression means 15A, 15B for ejaculating liquid from the tube member 9. The outer shell 2 of the device 1 is preferably covered by a coating of rubber, silicon, plastic or the like to provide for a more realistic, flesh-like feeling and sensation.

As shown in FIG. 2, the elongated upper member 4 has a substantially hollow interior 50. An upper end of the upper member 4 has an aperture 6 therethrough. The aperture 6 is preferably only large enough to allow a stream of liquid to be discharged, but various sizes and shapes of the opening may be used without interfering with the objectives of the invention. The elongated lower member 5 has a compartment 17 therein for receiving and holding one or more batteries 22 for powering the device 1. The compartment 17 is provided with conventional electrical connections for completing electrical circuits between the battery 22 and the various electrical components of the device 1 (described in further detail below). As shown in FIG. 1, the bottom end of the lower member 5 can be provided with are movable cap 30 for obtaining access to the battery compartment 17. In a preferred embodiment shown in FIGS. 2–4, the attachment means 3 is a threaded groove 3A on a lower end of the upper member 4 and a threaded groove 3B on an upper end of the lower member 5, the threaded grooves sized engage one another in threaded engagement. Alternatively, the means 3 could be snap mechanism or the like. An O-ring or other compressible ring maybe fitted at the juncture between the upper 4 and lower 5 members to prevent external liquids from entering the interior of the device 1 during use.

As shown in FIG. 5, the tube member 9 has a compressible liquid containment unit 11 on a lower end thereof. The liquid containment unit 11 is manufactured from a flexible material, such as vinyl, rubber, or the like, so as to allow for rapid compression of the outer walls of the liquid containment unit 11. A hollow neck member 40 extends upward from the liquid containment unit 11. The hollow neck member 40 is in fluid communication with the liquid containment unit 11. The neck member 40 has an open upper end 42. As shown in FIGS. 2 and 3, during use the tube member 9 is positioned inside the device 1 such that the open upper end 42 of the neck member 40 is inserted in the aperture 6 of the upper member 4. In one preferred embodiment, a lower end of the neck member 40 is threadably engaged to the liquid containment unit 11, such that the neck member 40 may be selectively removed from the liquid containment unit. The tube member 9 is preferably removable from the device 1, to facilitate cleaning of the device 1 and replacement of the tube member 9 as needed.

The compression means 15A, 15B is positioned in the device 1, preferably in the upper end of the lower member 5 as shown in FIG. 2. The compression means 15A, 15B is configured and positioned to compress the liquid containment unit 11 when electrical connection is selectively established between the compression means 15A, 15B and a battery 22 in the lower member 5. When the compression means 15A, 15B compresses the liquid containment unit 11, liquid 14 stored in the liquid containment 11 unit is ejaculated or projected through the open upper end 42 of the tube member 9. In a preferred embodiment shown in FIGS. 2, 3, 4, and 7, the compression means is a conventional DC powered solenoid pinch valve 15A, such as the type manufactured by Farmington Engineering, Inc., 7 Orchard Park Road, Madison Conn. 06443-2273. Such valves perform a forceful pinching action when electrical current is applied to the pinch valve. As shown most clearly in FIG. 3, the pinch valve 15A is fitted with pincer/pincher means 15B consisting preferably of a pair of arms 15B. Each arm 15B is attached to the pinch valve 15A such that when the pinch valve 15A performs a pinching action, the pinch valve 15A forcefully draws the arms 15B together. The pincer means 15B are preferably arcuate shaped so as to closely engage an outer surface of the liquid containment unit 11. The exact shape and configuration of the pincers 15B is not critical, provided that upon operation of the pinch valve 15A, the pincer arms 15B rapidly compress the liquid containment unit 11 with sufficient force to eject the liquid 14 from the tube member 9. As shown in FIG. 1, a means 102, such as a conventional button or external switch 102, can be provided on the outer side of the device 1, such as on the lower member 5, to allow a user to selectively close a switch to complete an electrical circuit between the battery and the compression means 15A and thereby selectively operate the compression means 15A.

Figure 9:
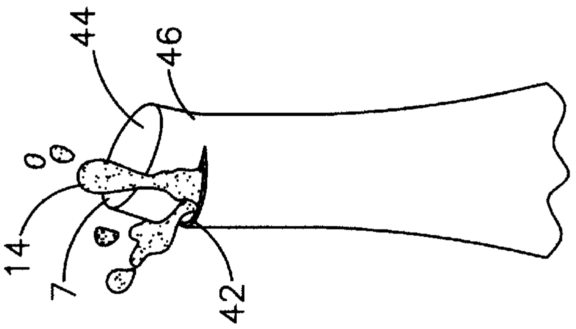
FIG. 9 is a side view of a top end of one embodiment of a tube member of the invention, showing the top end in an open position.
Figure 8:
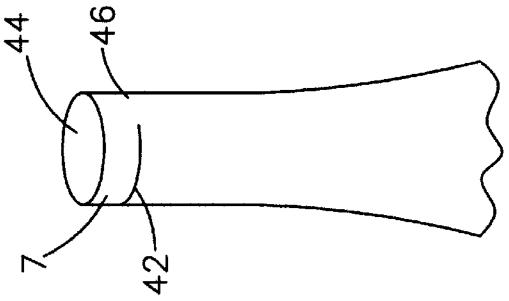
FIG. 8 is a side view of a top end of one embodiment of a tube member of the invention, showing the top end in a closed position.

A means is provided for maintaining the liquid 14 in the liquid containment unit 11 and/or neck member 40. The means may be the configuration of the tube member 9. As with bulb syringes, if the channel in the neck member 40 is sufficiently narrow, the pressure of the liquid 14 in the liquid containment unit 11 is sufficient to prevent air from entering the tube member 9 and displacing the liquid 14. Thus, even if the tube is inverted, the liquid 14 will not leak out, and will remain in the tube member 9 until the liquid containment unit 11 is compressed. Alternatively, the means may be a one-way pressure actuated valve 7. The one way valve 7 is preferably positioned in the aperture 6 or on the upper open end 42 of the neck member. The one-way valve 7 must have sufficient strength to hold itself shut until the liquid containment unit 11 is compressed, at which time the valve 7 must open to allow the liquid 14 to exit the tube member 9. The one-way valve 7 also preferably prevents the ejected liquid 14 from reentering the tube member 9. While numerous types of conventional one-way valves maybe used, a particularly economical valve 7 is shown in FIGS. 8 and 9. The valve 7 of FIGS. 8 and 9 consists of a slit opening 42 cut along the upper end of the neck member 40. In this embodiment, the neck member 40 has a closed upper end 44 and the slit 42 serves as the open upper end 42. With the neck member 40 composed of an elastic material such as rubber or plastic, the uncut portion 46 serves as a hinge having sufficient force to hold the valve 7 shut or generally shut against the neck member 40. As shown in FIG. 9, when liquid 14 is forced from the neck member 40 by compression of the liquid containment unit 11, the slit 42 opens sufficiently to allow the liquid 14 to be ejected from the tube member 9. Another economical one-way valve 7 is of the type commonly used on the caps of dishwashing liquid bottles. In a preferred embodiment, the configuration of the tube member 9 in conjunction with a one-way valve 7 serve together as the means for retaining liquid 14 in the tube member 9.

The device 1 is preferably provided with a vibration means 18, such as those found on conventional vibrators and dildos. The most commonly used vibration device is a "bullet" vibrating device, which consists primarily of a coil inside of a housing unit. The coil oscillates when DC current is applied to the device, thereby producing vibration. The vibration means 18 is positioned and configured to vibrate the device 1 when electrical connection is selectively established between the vibration means and a battery 22 in the lower member 5. In a preferred embodiment shown in FIGS.

2, 3 and 4, the vibration means 18 comprises one or more support members 60 extending upward from an upper end of the lower member 5, with a vibration unit positioned on an upper end of each the support member 60. As shown in FIG. 1, a means 104, such as a conventional button or external switch 104, can be provided on the outer side of the device 1, such as on the lower member 5, to allow a user to close a switch to complete an electrical circuit between the battery 22 and the vibration means 18 and thereby selectively operate the vibration means 18.

As shown in representational form in FIG. 4, the device 1 is preferably provided with a conventional timing unit 16. The timing unit 16 is electrically coupled to the compression means 15A. By setting the timing unit 16, the compression means 15A may be programmed to compress the liquid containment unit 11 (by opening DC current to the compression means 15A) upon expiration of a selected time interval. As shown in FIG. 1, a conventional timer control means 106, shown in representational form in FIG. 1, can be provided on the outer side of the device 1 to allow a user to program the timing unit 16. In another embodiment, the timer 16 may be provided with a random timer function, such that the timer 16 completes the circuit to the compression means 15A after a random time interval, thereby adding an element of surprise to the user(s) of the device. The timer 16 may be provided with both the programable function and the random timer function.

Figure 7:
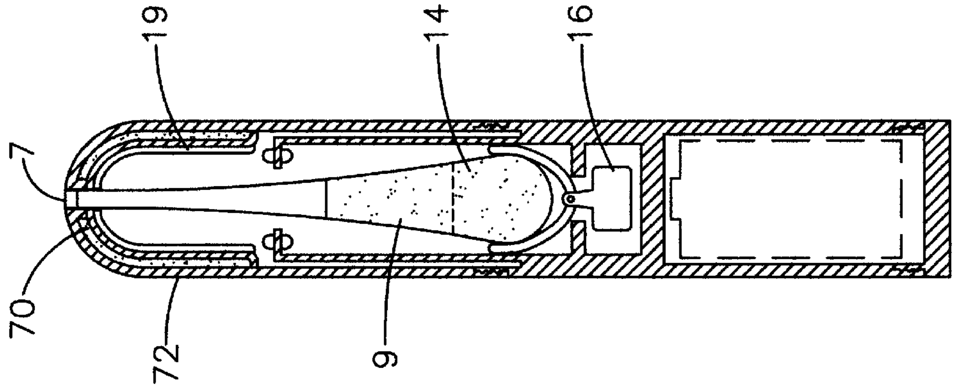
FIG. 7 is a cross-section side view of one embodiment of the invention, illustrating a gelatinous material contained in an inner compartment of the device.

As shown in FIG. 7, the device is preferably provided with a heating element 19. The heating element is preferably a cartridge heater, such as those manufactured by Watlow Electrical Manufacturing Company, 12001 Lackland Road, St. Louis, Mo. 63146. Cartridge heaters consist of a resistance wire encased in insulation and an outer sheath. A pair of leads are connected to the resistance wire. When DC current is applied to the cartridge heater via the leads, the resistance wire generates heat. The heating element 19 is positioned and configured to warm the upper member 4, and particularly the outer surface thereof, when electrical connection is selectively established between the heating unit 19 and a battery 22 in the lower member 5. As shown in FIG. 1, a means 108, such as a conventional button or external switch 108, can be provided on the outer side of the device 1, such as on the lower member 5, to allow a user to close a switch to complete an electrical circuit between the battery 22 and the heating element 19 and thereby selectively operate the heating element 19. As shown in FIG. 7, the device 1 can further be provided with a compartment 70 along an interior surface of at least an upper portion of the upper member, the compartment 70 containing and storing a gelatinous material 72, liquid, or other heat storage and transmission material. The compartment 70 is preferably configured to communicate with the heating element 19 such that the heating element warms the gelatinous material 72.

In operation, the sexual aid device of the invention is used to produce sexual stimulation by placing a liquid 14 in the liquid containment unit 11, placing a battery 22 in the lower member 5, placing the device in contact with a body part to be stimulated, and using the device to stimulate the body part, the parts to be stimulated generally being genitalia and anal regions. At a selected interval, the user can establish electrical connection between the battery 22 and the compression means 15 to thereby ejaculate the stored liquid 14 from the device 1. If the device is provided with a vibration means 18, a timing unit 16, or a heating element 19, the user can selectively use these features while stimulating the body part.

After use, the device 1 is preferably cleaned to remove body fluids and the like that may have accumulated in or on the device 1. The inner parts of the device can be cleaned by separating the upper member 4 from the lower member 5 to thereby open the device.

Although the present invention has been described in terms of specific embodiments, it is anticipated that alterations and modifications there of will no doubt become apparent to those skilled in the art. It is therefore intended that the following claims be interpreted as covering all alterations and modifications that fall within the true spirit and scope of the invention.

What is claimed is:

1. A sexual aid device for producing sexual stimulation comprising:

an elongated upper member, said upper member having a substantially hollow interior, an upper end of said upper member having an aperture therethrough;

an elongated lower member, said lower member having a compartment therein for receiving and holding one or more batteries for powering said device;

a means for removably securing said upper member to said lower member;

a tube member, said tube member having a compressible liquid containment unit on a lower end thereof, a hollow neck member extending upward from and in fluid communication with said liquid containment unit, said neck member having an open upper end;

said tube member positioned inside said device such that said open upper end of said neck member is inserted in said aperture of said upper member; and a compression means, said compression means configured and positioned to compress said liquid containment unit when electrical connection is selectively established between said compression means and a battery in said lower member, whereby a liquid stored in said liquid containment unit may be ejaculated through said open upper end of said tube member.

2. The device of claim 1, further comprising a vibration means in said device, said vibration means positioned and configured to vibrate said device when electrical connection is selectively established between said vibration means and a battery in said lower member.

3. The device of claim 2, further comprising a programable timing unit electrically coupled to said compression means, whereby said compression means may be programmed to compress said liquid containment unit upon expiration of a selected time interval.

4. The device of claim 3, further comprising a heating element in said device, said heating element positioned and configured to warm said upper member when electrical connection is selectively established between said heating element and a battery in said lower member.

5. The device of claim 2, further comprising a timing unit electrically coupled to said compression means, said timing unit capable of generating a random time interval such that said compression means may be programmed to compress said liquid containment unit upon expiration of said randomly generated time interval.

6. The device of claim 5, further comprising a heating element in said device, said heating element positioned and configured to warm said upper member when electrical connection is selectively established between said heating element and a battery in said lower member.

7. The device of claim 2, further comprising a heating element in said device, said heating element positioned and configured to warm said upper member when electrical connection is selectively established between said heating element and a battery in said lower member.

8. The device of claim 1, further comprising a programmable timing unit electrically coupled to said compression means, whereby said compression means may be programmed to compress said liquid containment unit upon expiration of a selected time interval.

9. The device of claim 8, further comprising a heating element in said device, said heating element positioned and configured to warm said upper member when electrical connection is selectively established between said heating element and a battery in said lower member.

10. The device of claim 1, further comprising a timing unit electrically coupled to said compression means, said timing unit capable of generating a random time interval such that said compression means may be programmed to compress said liquid containment unit upon expiration of said randomly generated time interval.

11. The device of claim 10, further comprising a heating element in said device, said heating element positioned and configured to warm said upper member when electrical connection is selectively established between said heating element and a battery in said lower member.

12. The device of claim 1, further comprising a heating element in said device, said heating element positioned and configured to warm said upper member when electrical connection is selectively established between said heating element and a battery in said lower member.

13. The device of claim 12, further comprising a compartment along an interior surface of at least an upper portion of said upper member, and a gelatinous material contained in said compartment.

14. The device of claim 13, wherein said compartment communicates with said heating element such that said heating element warms said gelatinous material.

15. The device of claim 1, wherein said tube member is removable from said device.

16. The device of claim 1, wherein a lower end of said neck member is threadably engaged to said liquid containment unit.

17. The device of claim 1, wherein said outer shell is covered by a coating selected from the group consisting of rubber, silicon, and plastic.

18. The device of claim 1, further comprising a one-way valve positioned in said aperture, said one-way valve allowing fluid in said tube member to exit said aperture while preventing said ejected liquid from reentering said aperture.

19. The device of claim 1, wherein said compression means is a solenoid pinch valve.

20. The device of claim 19, wherein said pinch valve has arcuate shaped pincers configured to closely engage an outer surface of said liquid containment unit.

21. A method for producing sexual stimulation comprising:

(a) providing a sexual aid device for producing sexual stimulation, said sexual aid device comprising:

(i) an elongated upper member, said upper member having a substantially hollow interior, an upper end of said upper member having an aperture therethrough; (ii) an elongated lower member, said lower member having a compartment therein for receiving and holding one or more batteries for powering said device; (iii) a means for removably securing said upper member to said lower member; (iv) a tube member, said tube member having a compressible liquid containment unit on a lower end thereof, a hollow neck member extending upward from and in fluid communication with said liquid containment unit, said neck member having an open upper end; (v) said tube member positioned inside said device such that said open upper end of said neck member is inserted in said aperture of said upper member; and (vi) a compression means, said compression means configured and positioned to compress said liquid containment unit when electrical connection is selectively established between said compression means and a battery in said lower member, whereby a liquid stored in said liquid containment unit may be ejaculated through said open upper end of said tube member;

(b) placing a liquid in said liquid containment unit and placing a battery in said lower member;

(b) placing said device in contact with a body part to be stimulated;

(c) using said device to stimulate said body part; and (d) at a selected interval, establishing electrical connection between said battery and said compression means to thereby ejaculate said stored liquid from said device.

22. The method of claim 21, further comprising said device having a vibration means therein, said vibration means positioned and configured to vibrate said device when electrical connection is selectively established between said vibration means and a battery in said lower member, and further comprising the step of establishing electrical connection between said battery and said vibration means to thereby vibrate said device.

23. The method of claim 21, further comprising said device having a timing unit electrically coupled to said compression means whereby said compression means may be programmed to compress said liquid containment unit upon expiration of a selected time interval, and further comprising the step of setting said timing unit to a selected time interval.

24. The method of claim 21, further comprising a timing unit electrically coupled to said compression means, said timing unit capable of generating a random time interval such that said compression means may be programmed to compress said liquid containment unit upon expiration of said randomly generated time interval.

25. The method of claim 21, further comprising said device having a heating element therein, said heating element positioned and configured to warn said liquid in said liquid containment unit when electrical connection is selectively established between said heating element and a battery in said lower member, and further comprising the step of establishing electrical connection between said battery and said heating element to thereby heat said device.

26. The method of claim 21, further comprising the steps of separating said upper member from said lower member to thereby open said device, and cleaning said open device.

* * * * *